United States Patent
Ding et al.

(10) Patent No.: US 11,540,872 B2
(45) Date of Patent: Jan. 3, 2023

(54) ELECTROSURGICAL INSTRUMENT WITH TRIGGER DRIVEN CUTTING FUNCTION

(71) Applicant: COVIDIEN LP, Mansfield, MA (US)

(72) Inventors: Weijiang Ding, Shanghai (CN); Kai Liu, Hunan (CN); Zaifeng Zhou, Shanghai (CN)

(73) Assignee: Covidien LP, Mansfield, MA (US)

( * ) Notice: Subject to any disclaimer, the term of this patent is extended or adjusted under 35 U.S.C. 154(b) by 783 days.

(21) Appl. No.: 16/493,665

(22) PCT Filed: Mar. 13, 2017

(86) PCT No.: PCT/CN2017/076386
§ 371 (c)(1),
(2) Date: Sep. 12, 2019

(87) PCT Pub. No.: WO2018/165808
PCT Pub. Date: Sep. 20, 2018

(65) Prior Publication Data
US 2020/0008863 A1  Jan. 9, 2020

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00595* (2013.01);
(Continued)

(58) Field of Classification Search
CPC .... A61B 2018/1457; A61B 2018/0063; A61B 2018/00607; A61B 2018/00601; A61B 2018/00595; A61B 18/1445
See application file for complete search history.

(56) References Cited

U.S. PATENT DOCUMENTS

D249,549 S  9/1978  Pike
D263,020 S  2/1982  Rau, III
(Continued)

FOREIGN PATENT DOCUMENTS

CN  201299462 Y  9/2009
CN  103841911  6/2014
(Continued)

OTHER PUBLICATIONS

EP17901164.8, Extended European Search Report, dated Oct. 21, 2020, 5pages.
(Continued)

*Primary Examiner* — Linda C Dvorak
*Assistant Examiner* — Ryan T Clark
(74) *Attorney, Agent, or Firm* — Carter, DeLuca & Farrell LLP

(57) ABSTRACT

An electrosurgical instrument (1) includes a first shaft member (110) pivotably coupled to a second shaft member (120), and a trigger (184) disposed on the second shaft member (120). The first and second shaft members (110,120) respectively include first and second handle members (130,140), and first and second jaw members (150,160). The first and second shaft members (110,120) define a longitudinal axis extending through a pivot, and first and second pivot axes that are substantially orthogonal to each other and the longitudinal axis. At least one of the first or second handle members (130,140) is pivotable about the first pivot axis to move the first and second jaw members (150,160) to an open position, a grasping position, or a sealing position. The trigger (184) is movable to pivot at least one of the first or second shaft members (110,120) about the second pivot axis to laterally displace the first and second jaw members (150,160) relative to each other to a cutting position.

17 Claims, 9 Drawing Sheets

(52) U.S. Cl.
CPC ............ *A61B 2018/00601* (2013.01); *A61B 2018/00607* (2013.01); *A61B 2018/00916* (2013.01); *A61B 2018/1457* (2013.01)

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 10,779,881 B2 * | 9/2020 | Twomey ............ A61B 18/1442 |
| 2002/0107517 A1 * | 8/2002 | Witt .................. A61B 18/1442 606/50 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | |
|---|---|---|
| CN | 106063723 | 11/2016 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 02 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 02 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |

(56) References Cited

FOREIGN PATENT DOCUMENTS

| | | |
|---|---|---|
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Heniford et al. "Initial Research and Clinical Results with an Electrothermal Bipolar Vessel Sealer" Oct. 1999.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surger" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

U.S. Appl. No. 08/926,869, filed Sep. 10, 1997; inventor: James G. Chandler, Abandoned.

U.S. Appl. No. 09/177,950, filed Oct. 23, 1998; inventor: Randel A. Frazier, abandoned.

U.S. Appl. No. 09/387,883, filed Sep. 1, 1999; inventor: Dale F. Schmaltz, abandoned.

U.S. Appl. No. 09/591,328, filed Jun. 9, 2000; inventor: Thomas P. Ryan, abandoned.

U.S. Appl. No. 12/336,970, filed Dec. 17, 2008; inventor: Paul R. Sremeich, abandoned.

U.S. Appl. No. 14/065,644, filed Oct. 29, 2013; inventor: Reschke, abandoned.

\* cited by examiner

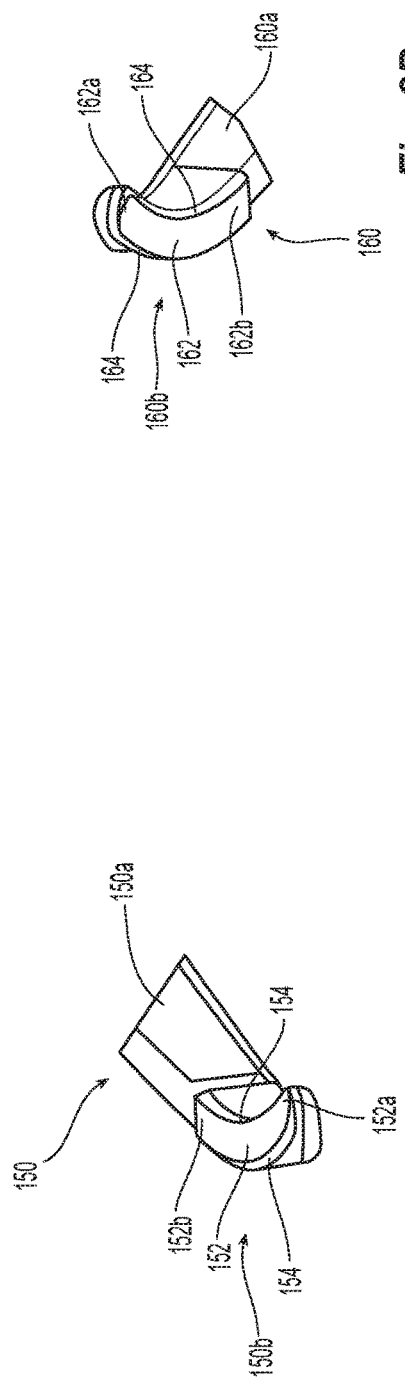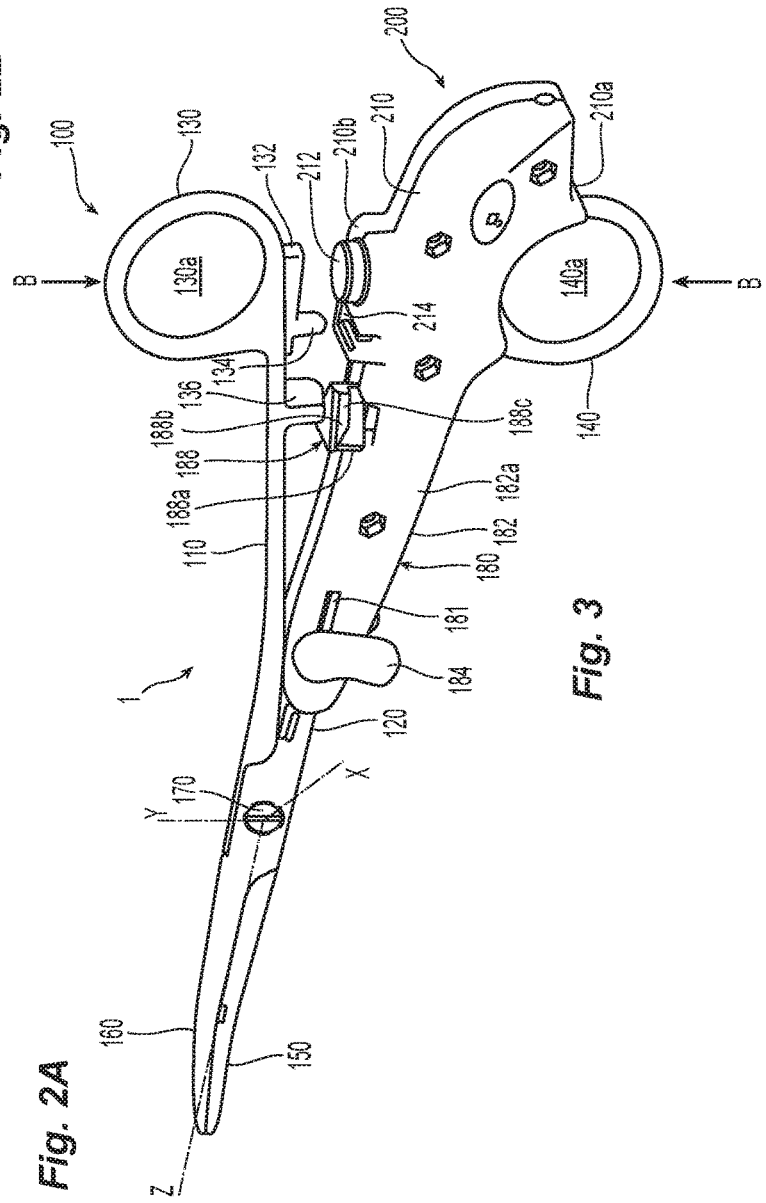

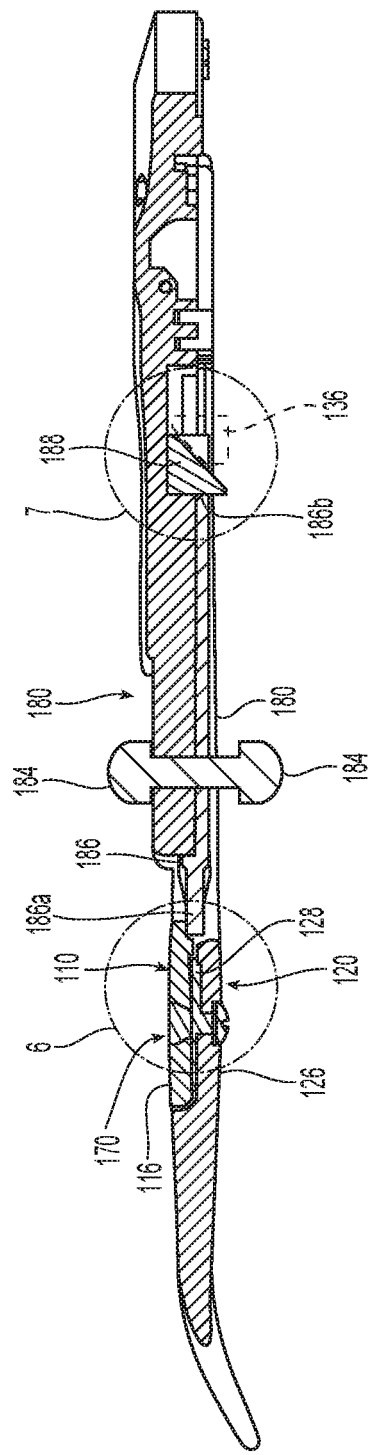
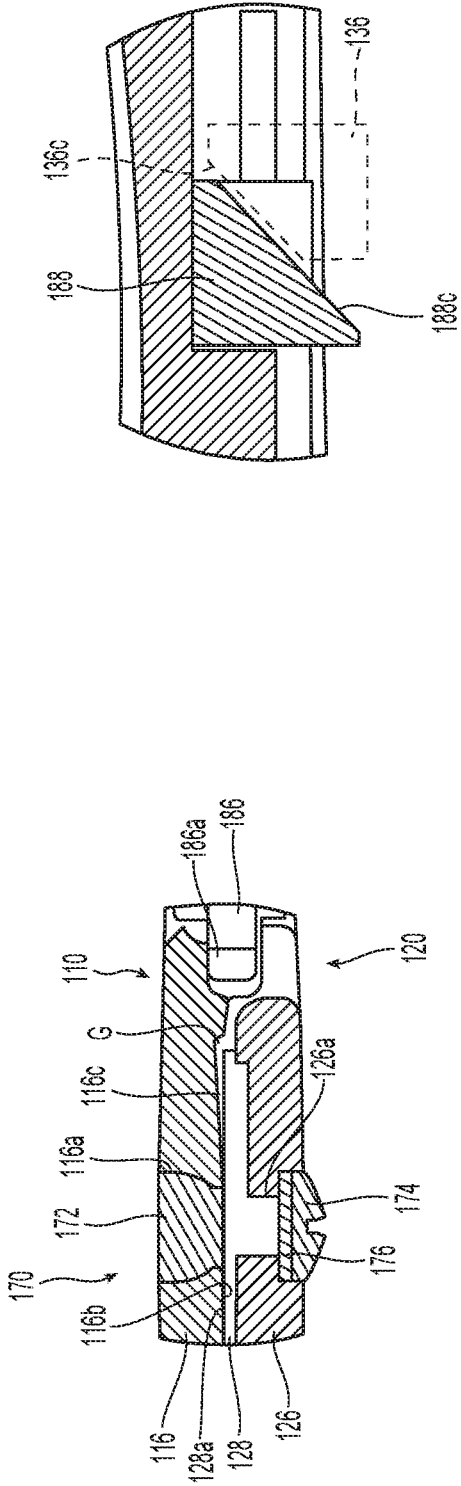

ELECTROSURGICAL INSTRUMENT WITH TRIGGER DRIVEN CUTTING FUNCTION

BACKGROUND

1. Background of Related Art

The present disclosure relates to electrosurgical instruments and, more particularly, to an electrosurgical forceps configured for grasping, treating, and/or cutting tissue.

2. Technical Field

A forceps or hemostat is a surgical plier-like instrument which relies on mechanical action between its jaws to grasp, clamp, and constrict tissue. Energy-based forceps utilize both mechanical clamping action and energy, e.g., electrosurgical energy, ultrasonic energy, light energy, microwave energy, heat, etc., to affect hemostasis by heating tissue to coagulate and/or cauterize tissue. Certain surgical procedures require more than simply cauterizing tissue and rely on the unique combination of clamping pressure, precise energy control, and gap distance (i.e., distance between opposing jaws when closed about tissue) to "seal" tissue. Typically, once tissue is sealed, the surgeon has to accurately sever the tissue along the newly formed tissue seal. Accordingly, many tissue sealing instruments have been designed to incorporate a blade that is movable with respect to a blade slot disposed in a jaw of the tissue sealing instrument to sever the tissue after forming a tissue seal.

Tissue sealing instruments that include a blade and blade slot, however, are typically single-use devices as the blade and blade slot may be difficult to clean, and the blade may wear and dull with repeated use. The incorporation of a blade slot into a jaw of a tissue sealing instrument may reduce the sealing strength of the jaw, and the width of the blade slot may increase the width of the jaw which, in turn, may result in a reduction in the dissection capabilities of the tissue sealing instrument.

SUMMARY

The present disclosure is directed to reusable electrosurgical instruments including movable, opposed jaw members that are configured for grasping, sealing, and/or cutting without the use of a blade and slot jaw configuration. The reusable electrosurgical instruments have a handle assembly that allows an operator to effect grasping and/or sealing of tissue between the jaw members by effecting linear finger movements, and cutting of tissue between the jaw members by actuation of a trigger. This configuration reduces finger fatigue, improves ergonomics, and/or increases operator control of the jaw members.

In accordance with aspects of the present disclosure, an electrosurgical instrument includes a first shaft member coupled to a second shaft member about a pivot, and a trigger assembly disposed on the second shaft member. The first shaft member includes a proximal portion having a first handle member and a distal portion including a first jaw member, and the second shaft member includes a proximal portion having a second handle member and a distal portion including a second jaw member. The trigger assembly includes a housing supporting a trigger that is movable relative to the housing. The first and second shaft members define a longitudinal axis extending through the pivot, and first and second pivot axes that are substantially orthogonal to each other and the longitudinal axis. At least one of the first or second handle members is pivotable about the first pivot axis to move the first and second jaw members, which are disposed in opposed and aligned relation to each other, to an open position, a grasping position, or a sealing position. The trigger is movable to pivot at least one of the first or second shaft members about the second pivot axis to laterally displace the first and second jaw members relative to each other to a cutting position.

In some aspects, the trigger is longitudinally slidable relative to the housing between a proximal position and a distal position. In certain aspects, the trigger is biased in the distal position.

In aspects, the trigger assembly includes a longitudinal bar disposed within the housing and secured to the trigger such that longitudinal movement of the trigger causes a corresponding longitudinal movement of the longitudinal bar. The longitudinal bar may include a distal end portion movable in and out of engagement with intersection portions of the first and second shaft members. In some aspects, when the trigger is disposed in the distal position, the distal end portion of the longitudinal bar is disposed between the intersection portions of the first and second shaft members such that the first and second shaft members are only pivotable about the first pivot axis. In some aspects, when the trigger is disposed in the proximal position, the distal end portion of the longitudinal bar is proximal to the intersection portions of the first and second shaft members such that the first and second shaft members are pivotable about the first and second pivot axes.

In aspects, the first shaft member includes a first guide member and the longitudinal bar of the trigger assembly includes a proximal end portion having a second guide member movable in and out of engagement with the first guide member. The first and second guide members may each have an angled wall having complementary slopes. In some aspects, the angled walls are disposed in opposed spaced relation relative to each other when the first and second jaw members are disposed in the sealing position and the trigger is disposed in the distal position. In some aspects, when the trigger is actuated to the proximal position, the angled walls of the first and second guide members slidably engage each other and a force produced by proximal movement of the second guide member against the first guide member moves the first shaft member about the second pivot axis.

The first and second guide members may each include a body portion and a leg portion having complementary L-shaped configurations. The leg portions of the first and second guide members may be configured to engage each other and limit movement of the first shaft member about the first pivot axis when the trigger is actuated to the proximal position.

In aspects, the electrosurgical instrument includes a connector assembly including a housing selectively engageable with the second elongated shaft member. The connector assembly is configured to communicate electrosurgical energy between the first and second jaw members when in the sealing position.

In some aspects, the first and second jaw members each include a tissue contacting surface having a shear edge.

The pivot may extend through intersection portions of the first and second shaft members. In some aspects, the intersection portions each include a substantially flat distal portion that is substantially flush with one another when the at least one of the first or second handle members is pivoted about the first pivot axis. In some aspects, the intersection portion of the first shaft member includes an angled proximal portion defining a gap between the intersections portions, and when the at least one of the first or second shaft members is pivoted about the second pivot axis, the gap is closed. In certain aspects, the intersection portion of the second shaft member includes an insulative shim.

In accordance with aspects of the present disclosure, a method of treating tissue includes: pivoting at least one of first or second handle members of respective first or second shaft members of an electrosurgical instrument about a first pivot axis that is orthogonal to a longitudinal axis defined through a pivot of the electrosurgical instrument to effect movement of first and second jaw members of the electrosurgical instrument to a sealing position in which the first and second jaw members are opposed and aligned with one another; and actuating a trigger supported on a housing of a trigger assembly disposed on the second shaft member of the electrosurgical instrument to pivot at least one of the first or second shaft members about a second pivot axis that is transverse, e.g., orthogonal, to the first pivot axis and the longitudinal axis to effect movement of the first and second jaw members from the sealing position to a cutting position in which the first and second jaw members are laterally displaced with respect to one another.

Other aspects, features, and advantages will be apparent from the description, drawings, and the claims.

BRIEF DESCRIPTION OF THE DRAWINGS

Various aspects and features of the present disclosure are described herein with reference to the drawings wherein corresponding reference characters indicate corresponding parts throughout the drawings, and wherein:

FIGS. 2A and 2B are enlarged, perspective views of portions of the electrosurgical instrument of FIG. 1, shown along the areas of detail 2A and 2B, respectively, in FIG. 1;

FIG. 3 is a side, perspective view of the electrosurgical instrument of FIG. 1 in a closed position;

FIG. 5 is a cross-sectional view of the electrosurgical instrument of FIGS. 3 and 4, taken along line 5-5 of FIG. 4;

FIG. 6 is an enlarged view of a portion of the electrosurgical instrument of FIGS. 3-5, shown along the area of detail 6 in FIG. 5;

FIG. 7 is an enlarged view of a portion of the electrosurgical instrument of FIGS. 3-5, shown along the area of detail 7 in FIG. 5;

DETAILED DESCRIPTION

In this disclosure, the term "proximal" refers to a portion of a structure closer to an operator, while the term "distal" refers to a portion of the same structure further from the operator. As used herein, the term "subject" refers to a human patient or animal. The term "operator" refers to a doctor (e.g., a surgeon), a nurse, and other clinicians or care providers, and may include support personnel. The terms "generally," "substantially," and "about" shall be understood as words of approximation that take into account relatively little variation in the modified term(s). Reference terms, such as "horizontal," "vertical," "upper," "lower," "top," "bottom," and the like, are intended to ease description of the embodiments and are not intended to have any limiting effect on the ultimate orientations of the surgical instruments, or any parts thereof.

Figure 1:
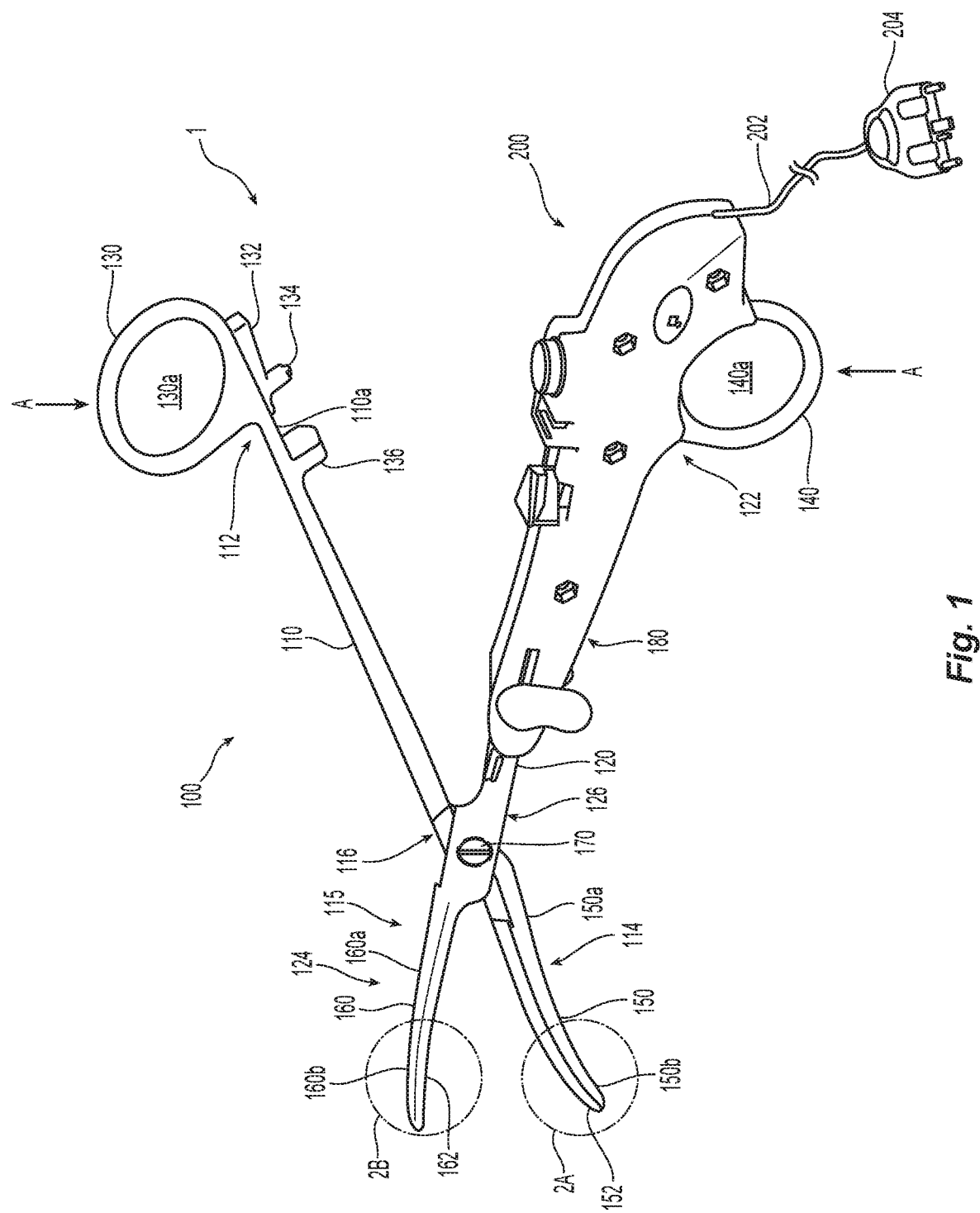
FIG. 1 is a side, perspective view of an open, assembled electrosurgical instrument including a forceps and a connector assembly in accordance with the present disclosure.

Referring now to FIG. 1, an energy-based surgical instrument 1 in accordance with the present disclosure is configured for grasping, electrically treating, and mechanically dissecting tissue or vessels in open and/or laparoscopic surgical procedures. The electrosurgical instrument 1 includes a reusable forceps 100 and a disposable connector assembly 200 removably attachable to the forceps 100. The connector assembly 200 is releasably connected to an electrosurgical energy source 300 (FIG. 4) via a cable 202 terminating at a plug 204. Alternatively, the connector assembly 200 may be reusable.

The forceps 100 includes a first elongated shaft member 110 and a second elongated shaft member 120. The first elongated shaft member 110 includes proximal and distal portions 112, 114, respectively, and the second elongated shaft member 120 includes proximal and distal portions 122, 124, respectively. The first and second shaft members 110, 120 intersect at respective intersection portions 116, 126 that are pivotably coupled together via a pivot pin 170 such that the first and second shaft members 110, 120 are movable relative to each other. The forceps 100 is movable between an open position (see e.g., FIG. 1), a closed or grasping position (see e.g., FIG. 3), a sealing position (see e.g., FIG. 8), and a cutting position (see e.g., FIG. 11), as described in further detail below.

The proximal portions 112, 122 of the first and second shaft members 110, 120 include first and second handle members 130, 140, respectively. The first and second handle members 130, 140 are configured to allow an operator to effect movement of one or both of the first and second shaft members 110, 120 relative to the other. The first and second handle members 130, 140 each define a finger hole 130*a*, 140*a*, respectively, therethrough for receiving a finger of an operator. The finger holes 130*a*, 140*a* facilitate movement of the first and second handle members 130, 140 relative to each other. The first and second handle members 130, 140 are each monolithically formed with respective first and second shaft members 110, 120. Alternatively, the first and second handle members 130, 140 may each be engaged with respective first and second shaft members 110, 120 in any suitable configuration, e.g., via mechanical engagement, molding, adhesion, etc.

The proximal portion 112 of the first shaft member 110 includes a bumper 132 and a connector pin 134, each extending from an inner surface 110*a* of the first shaft member 110 towards the second handle member 140. The proximal portion 112 of the first shaft member 110 further includes a first guide member 136 extending from the inner surface 110a of the first shaft member 110 and disposed distal to, and in spaced relation from, the connector pin 134 and the bumper 132.

The proximal portion 122 of the second shaft member 120 is configured to releasably engage the connector assembly 200 and includes a trigger assembly 180 disposed thereon, as described in further detail below.

With continued reference to FIG. 1, the distal portions 114, 124 of the first and second shaft members 110, 120 cooperate to define an end effector assembly 115 having opposed first and second jaw members 150, 160. The first and second jaw members 150, 160 extend distally from the respective intersection portions 116, 126 of the first and second shaft members 110, 120. Proximal portions 150a, 160a of the first and second jaw members 150, 160 extend longitudinally from the intersection portions 116, 126 along a longitudinal axis "z" (FIG. 3) defined through the forceps 100 and passing through a center of the pivot pin 170. Distal portions 150b, 160b of the first and second jaw members 150, 160 include respective first and second tissue contacting surfaces 152, 162 that are opposed to one another and distally extend longitudinally and laterally away from the longitudinal axis "z" (FIG. 3).

As shown in FIGS. 2A and 2B, in conjunction with FIG. 1, the first and second tissue contacting surfaces 152, 162 of the distal portions 150b, 160b of the first and second jaw members 150, 160 are twisted (e.g., curved, curled, bent, or otherwise shaped) with respect to the proximal portions 150a, 160a of the first and second jaw members 150, 160. The first and second tissue contacting surfaces 152, 162 each include a leading end portion 152a, 162a that is distal to a trailing end portion 152b, 162b, and shear edges 154, 164 at opposed sides of the first and second tissue contacting surfaces 152, 162, respectively.

Figure 8:
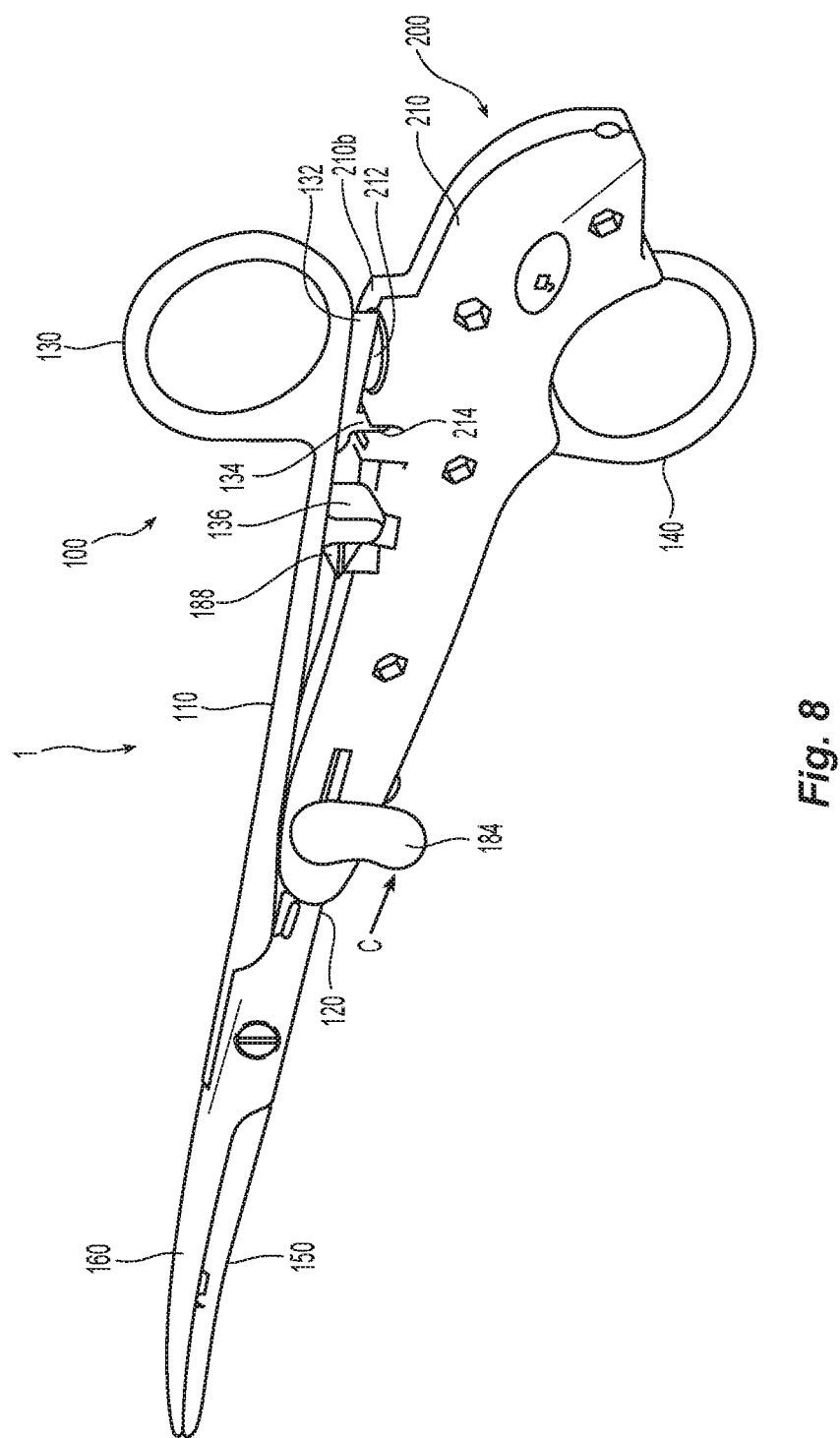
FIG. 8 is a side, perspective view of the electrosurgical instrument of FIG. 1 in a sealing position.
Figure 11:
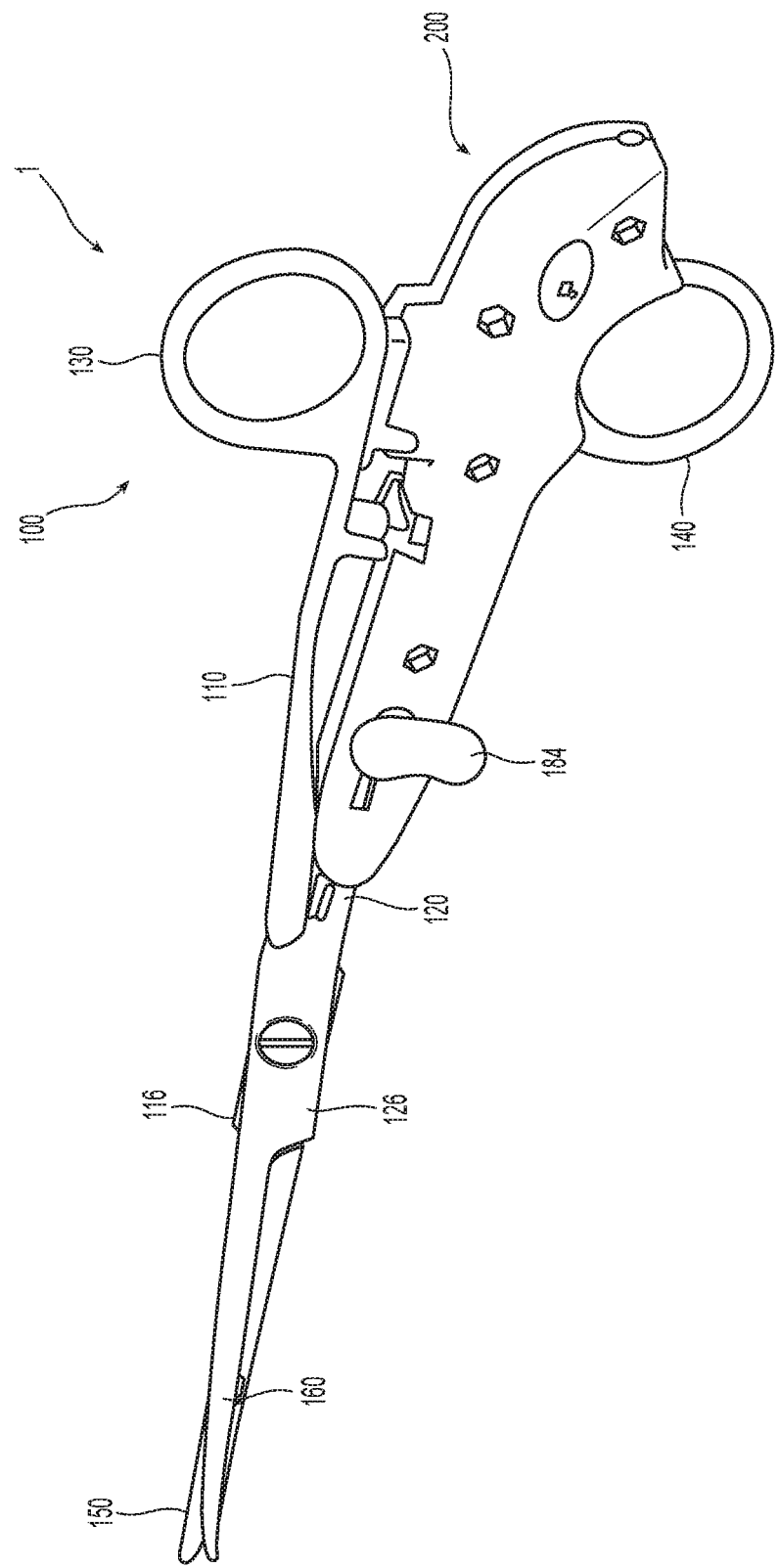
FIG. 11 is a side, perspective view of the electrosurgical instrument of FIG. 1 in a cutting position.
Figure 13:
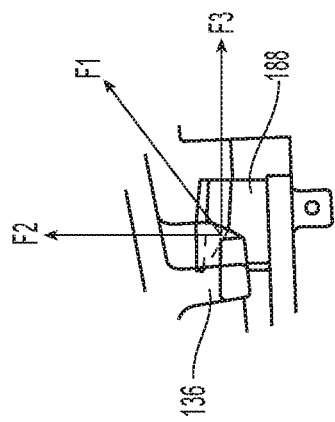
FIG. 13 is an enlarged view of a portion of the electrosurgical instrument of FIGS. 11 and 12, shown along the area of detail 13 in FIG. 12.

The first and second tissue contacting surfaces 152, 162 have complementary geometries such that when the first and second jaw members 150, 160 are in the grasping position of FIG. 3 or the sealing position of FIG. 8, the first and second tissue contacting surfaces 152, 162 are opposed and aligned for grasping and/or sealing tissue disposed therebetween, and when in the cutting position of FIG. 11, the first and second tissue contacting surfaces 152, 162 are laterally offset with respect to each other with increased clearance at the leading end portions 152a, 162a of the first and second tissue contacting surfaces 152, 162 for cutting tissue.

The tissue contacting surfaces 152, 162 of the first and second jaw members 150, 160 may have other configurations for grasping, sealing, and/or cutting tissue, such as, for example, having complementary stepped sealing surfaces defining shear edges therebetween.

Figure 4:
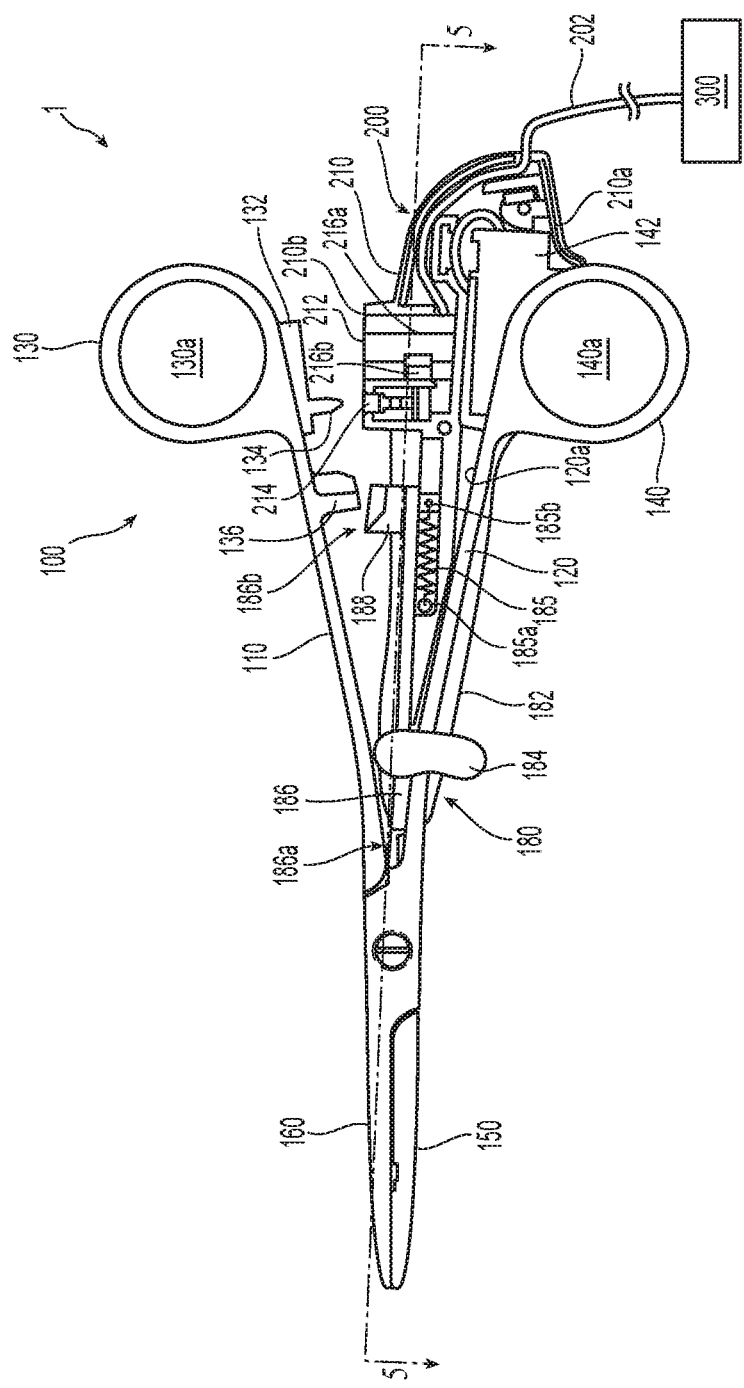
FIG. 4 is a side view of the electrosurgical instrument of FIG. 3, with housing parts removed.

Referring now to FIGS. 3 and 4, the connector assembly 200 includes a housing 210 including a lower surface 210a configured to engage a raised rail 142 extending from an inner surface 120a of the second shaft member 120. The lower surface 210a may be contoured to facilitate an ergonomic fit with a finger of an operator positioned through the finger hole 140a of the second handle member 140. The housing 210 of the connector assembly 200 may be slid distally and proximally along the raised rail 142 to respectively secure and release the connector assembly 200 relative to the forceps 100.

The housing 210 includes an upper surface 210b including a switch or power button 212 disposed in general alignment with the bumper 132 of the first handle member 130. The upper surface 210b of the housing 210 further defines an opening 214 in general alignment with the connector pin 134 of the first handle member 130.

The forceps 100 is formed of a conductive material, such as a metal, and includes an electrically insulative coating disposed over the forceps 100, except at the tissue contacting surfaces 152, 162 (FIG. 1) of the first and second jaw members 150, 160, the connector pin 134 of the first handle member 130, and the raised rail 142 of the second handle member 140. Accordingly, the tissue contacting surfaces 152, 162, the connector pin 134, and the raised rail 142 are not coated with an insulative material and are electrically conductive.

With continued reference to FIG. 4, first and second conductive members 216a, 216b are disposed within the housing 210 of the connector assembly 200, with the second conductive member 216b coupled to a portion of the raised rail 142. The connector pin 134 of the first shaft member 110 is movable into contact with the second conductive member 216b, and the first conductive connector member 216a is movable into contact with the second conductive connector member 216b in response to movement (e.g., depression) of the power button 212. The power button 212 is electrically connected to an electrosurgical energy source 300, such as an RF generator, such that contact between the first and second conductive members 216a, 216b closes an electrical circuit and energizes the tissue contacting surfaces 152, 162 (FIG. 1) of the first and second jaw members 150, 160.

The connector assembly 200 may have other configurations for activating and energizing the first and second jaw members 150, 160, as is within the purview of those skilled in the art.

Referring now to FIGS. 5 and 6, the pivot pin 170 is positioned through aligned openings 116a, 126a defined in the respective intersection portions 116, 126 of the first and second shaft members 110, 120, as well as through an insulative shim 128 disposed between the intersection portions 116, 126. The insulative shim 128 is dimensioned to extend along the intersection portions 116, 126 of the first and second shaft members 110, 120 and to electrically isolate the first and second shaft members 110, 120 from each other. The insulative shim 128 is formed from an electrically insulative material, such as a ceramic or plastic, and may be glued, brazed, or otherwise mechanically and/or chemically secured to the second shaft member 120, as is within the purview of those skilled in the art. Additionally or alternatively, an insulative coating, e.g., a ceramic coating, may be disposed between the intersection portions 116, 126 of the first and second shaft members 110, 120 (e.g., coated on an inner surface of intersection portion 126 of the second shaft member).

The insulative shim 128 includes a substantially flat outer surface 128a facing the intersection portion 116 of the first shaft member 110. The intersection portion 116 of the first shaft member 110 includes a substantially flat distal inner surface 116b and an angled proximal inner surface 116c that tapers proximally and outwardly, and defines a gap "G" between the first shaft member 110 and the insulative shim 128.

The pivot pin 170 includes a substantially semispherical head 172 disposed in the opening 116a of the first shaft member 110 and a cylindrical shaft 174 extending through the insulative shim 128 and the opening 126a defined in the second shaft member 120. A flange member 176 is disposed within the opening 126a of the second shaft member 120 and over the cylindrical shaft 174 to secure the pivot pin 170 to the first and second shaft members 110, 120.

As best seen in FIGS. 3 and 6, the pivot pin 170 defines pivot axes "x" and "y" which are substantially orthogonal to the longitudinal axis "z" of the forceps 100 and to each other, and about which the first and/or second shaft members 110, 120 are pivotable. The distal inner surface 116b of the intersection portion 116 of the first shaft member 110 and the outer surface 128a of the insulative shim 128 are substantially flush with each other to allow the first and second shaft members 110, 120 to rotate about the "x" axis when moving between the open position (FIG. 1), the grasping position (FIG. 3), and the sealing position (FIG. 8). The proximal inner surface 116c of the intersection portion 116 of the first shaft member 110 and the outer surface 128a of the insulative shim 128 allow the first and second shaft members 110, 120 to rotate about the "y" axis in the range defined by the gap "G" when moving to the cutting position (FIG. 11).

Referring again to FIGS. 3-5, the trigger assembly 180 includes a housing 182 supporting a trigger 184 on an outer surface 182a of the housing 182. The trigger 184 is longitudinally slidable relative to the housing 182 through opposed and aligned through holes 181 defined in the housing 182 between a distal position (FIG. 3) and a proximal position (FIG. 11). The trigger 184 may be any actuator within the purview of those skilled in the art such as, for example, finger-controlled buttons and knobs, among other slidable members to activate the cutting function of the forceps 100.

As best seen in FIGS. 4 and 5, the housing 182 of the trigger assembly 180 houses a longitudinal bar 186 that is secured to the trigger 184 such that longitudinal movement of the trigger 184 results in a corresponding longitudinal movement of the longitudinal bar 186. A biasing member 185, such as a coil spring, includes a first end 185a secured to the longitudinal bar 186 and a second end 185b secured to the housing 182 to bias the longitudinal bar 186 and thus, the trigger 184, in the distal position.

The longitudinal bar 186 includes a distal end portion 186a configured to move in and out of engagement with the intersection portions 116, 126 of the first and second shaft members 110, 120, and a proximal end portion 186b including a second guide member 188 configured to move in and out of engagement with the first guide member 136 of the first shaft member 110.

Figure 12:
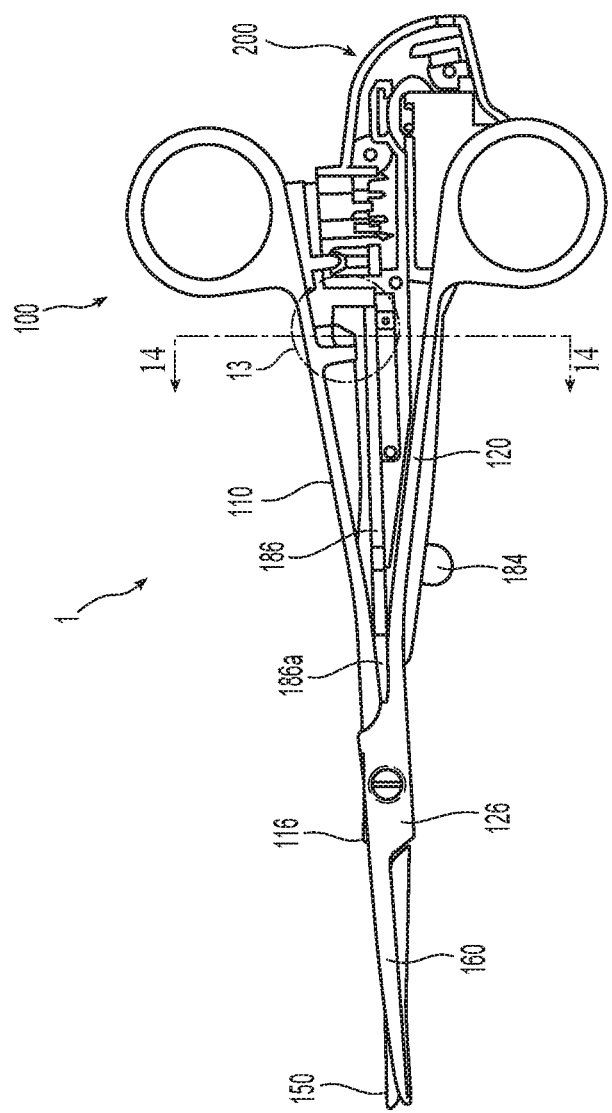
FIG. 12 is a side view of the electrosurgical instrument of FIG. 11, with housing parts removed.

When the trigger 184 is disposed in the distal position, as shown, for example, in FIGS. 5 and 6, the distal end portion 186a of the longitudinal bar 186 is disposed between the intersection portions 116, 126 of the first and second shaft members 110, 120 thereby allowing the first and second shaft members 110, 120 to pivot about the "x" axis (FIG. 3) while preventing movement of the first and second shaft members 110, 120 about the "y" axis (FIG. 3). When the trigger 184 is disposed in the proximal position, as shown, for example, in FIGS. 11 and 12, the distal end portion 186a of the longitudinal bar 186 is proximal to, and not engaged with, the intersection portions 116, 126 of the first and second shaft members 110, 120 thereby allowing the first and second shaft members 110, 120 to pivot about the "x" and/or "y" axes (FIG. 3).

Figure 10:
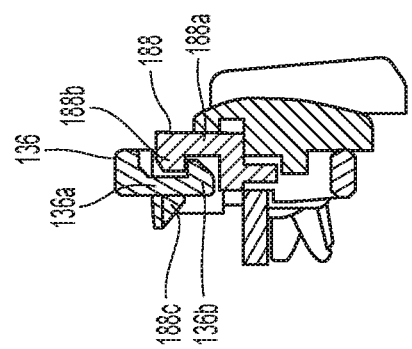
FIG. 10 is a cross-sectional view of the electrosurgical instrument of FIGS. 8 and 9, taken along line 10-10 of FIG. 9.

As best seen in FIGS. 3, 7, and 10, the second guide member 188 extends out of the housing 182 of the trigger assembly 180 in substantial alignment with the first guide member 136 of the first shaft member 110. The second guide member 188 includes a body portion 188a extending generally vertically towards the first shaft member 110 and a leg portion 188b extending substantially perpendicularly from the body portion 188a such that the body portion 188a and the leg portion 188b have a general L-shaped configuration (see e.g., FIG. 10). The body portion 188a and the leg portion 188b of the second guide member 188 are disposed at an angle with respect to the longitudinal axis "z" (FIG. 3) of the forceps 100, and the leg portion 188b includes an angled wall 188c.

Similarly, with continued reference to FIGS. 7 and 10, the first guide member 136 includes a body portion 136a extending generally vertically towards the second shaft member 120 and a leg portion 136b extending substantially perpendicularly from the body portion 136a such that the body portion 136a and the leg portion 136b have a general L-shaped configuration. The body portion 136a and the leg portion 136b of the first guide member 136 is disposed at an angle with respect to the longitudinal axis "z" (FIG. 3) of the forceps 100, and the body portion 136a includes an angled wall 136c (shown in phantom in FIG. 7). The general L-shaped configurations of the first and second guide members 136, 188 are complementary to each other, and the angled walls 136c, 188c of the first and second guide members 136, 188 have complementary slopes such that the leg portions 136b, 188b are configured to engage each other and the angled walls 136c, 188c are configured to contact and slide relative to each other.

Figure 9:
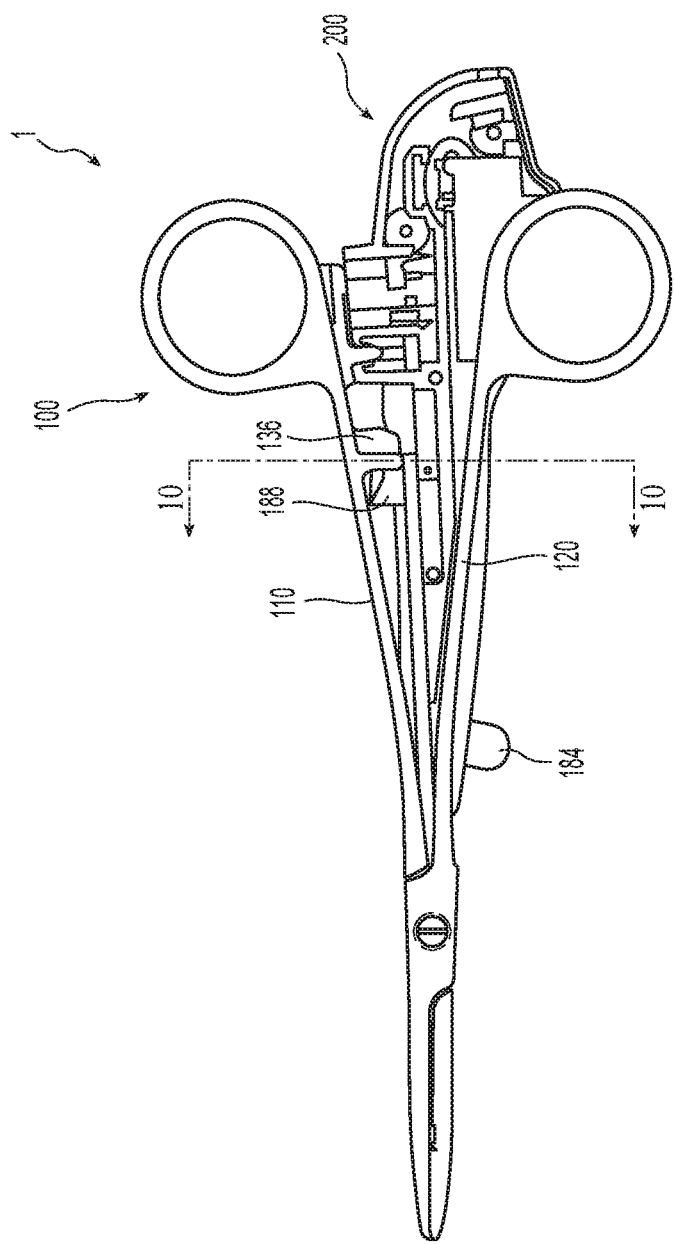
FIG. 9 is a side view of the electrosurgical instrument of FIG. 8, with housing parts removed.
Figure 14:
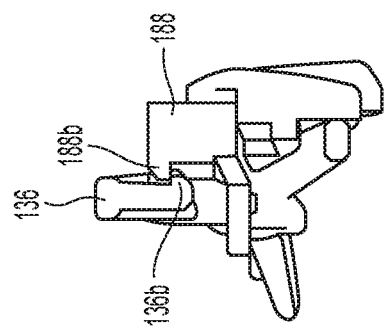
FIG. 14 is a cross-sectional view of the electrosurgical instrument of FIGS. 11 and 12, taken along line 14-14 of FIG. 12.

When the forceps 100 is in the sealing position as shown in FIGS. 8-10, and the trigger 184 is in the distal position, the first guide member 136 is aligned with a proximal portion of the second guide member 188 such that the angled walls 136c, 188c are disposed in opposed spaced relation relative to each other (FIG. 7). When the forceps 100 is in the cutting position as shown in FIGS. 11-14, and the trigger 184 is in the proximal position, the first guide member 136 is engaged with a distal portion of the second guide member 188. Specifically, during movement of the forceps 100 from the sealing position to the cutting position, the trigger 184 is slid proximally which, in turn, compresses the biasing member 185 and longitudinally translates the longitudinal bar 186 and thus, the second guide member 188, proximally. The angled wall 188c of the second guide member 188 contacts and slides against the angled wall 136c of the first guide member 136, exerting forces "F1"-"F3" (FIG. 13) against the first guide member 136. The forces "F1"-"F3" cause the first guide member 136 to elastically deform and pivot the first shaft member 110 about the "x" and "y" axes (FIG. 3). The movement about the "x" axis, however, is limited by the contact between the leg portions 136b, 188b of the first and second guide members 136, 188, as shown in FIG. 14.

In an example method of using the assembled forceps 100 for grasping, sealing, and/or cutting tissue, the forceps 100 is placed at a desired surgical site adjacent desired tissue and/or vessel(s) with the first and second jaw members 150, 160 disposed in an open position shown, for example, FIG. 1. The first and second handle members 130, 140 are approximated from the open position to a closed position shown in FIG. 3, by moving at least one of the first and second handle members 130, 140 towards the other in the direction of arrows "A" shown in FIG. 1 such that the first and second handle members 130, 140 pivot with respect to the other about the pivot pin 170 about the "x" axis to grasp tissue between the first and second jaw members 150, 160. The first and second jaw members 150, 160 are aligned and opposed to one another during rotation about the "x" axis, and the complementary geometry of the tissue contacting surfaces 152, 162 (FIG. 1) allow the first and second jaw members 150, 160 to firmly grasp the tissue therebetween.

As discussed above, the first and second handle members 130, 140 only rotate about the "x" axis during movement between the open and closed positions as the trigger 184 is biased in the distal position such that the distal end portion 186*a* of the longitudinal bar 186 of the trigger assembly 180 is positioned between the intersection portions 116, 126 of the first and second shaft members 110, 120 thereby preventing movement about the "y" axis.

To seal the tissue disposed between the first and second jaw members 150, 160, at least one of the first and second handle members 130, 140 is moved towards the other in the direction of arrows "B" shown in FIG. 3 such that the first and second handle members 130, 140 further pivot with respect to the other about the pivot pin 170 about the "x" axis to the sealing position shown in FIG. 8. As discussed above, the first and second handle members 130, 140 only rotate about the "x" axis during movement between the grasping and sealing positions as the trigger 184 is biased in the in the distal position.

This movement to the sealing position causes the bumper 132 of the first handle member 130 to depress the power button 212 of the connector assembly 200 while the connector pin 134 enters the housing 210 of the connector assembly 200 through the opening 214 defined in the upper surface 210*b* of the housing 210. As discussed above, activation of the power button 212 closes the electrical circuit and energizes the tissue contacting surfaces 152, 162 (FIG. 1) of the first and second jaw members 150, 160 to seal the tissue disposed therebetween. Sealing is effected, for example, by the application of pressure on tissue disposed between the first and second tissue contacting surfaces 152, 162 of the first and second jaw members 150, 160, and the electrosurgical energy transferred from the electrosurgical energy source 300.

When sealing is complete, the first and second handle members 130, 140 may be returned to the open position to release the tissue or may be moved to the cutting position shown in FIG. 11 to cut the tissue disposed between the first and second jaw members 150, 160. The forceps 100 is moved to the cutting position by sliding the trigger 184 proximally, in the direction of arrow "C" shown in FIG. 8, towards the second handle member 140 of the second shaft member 120. Proximal movement of the trigger 184 causes the first shaft member 110 to pivot about the pivot pin 170 about the "y" axis which, in turn, causes a corresponding movement of the bumper 132 and the connector pin 134 such that the bumper 132 releases the power button 212 and the connector pin 134 traverses the opening 214 of the housing 210. At the same time, the tissue contacting surfaces 152, 162 (FIG. 1) of the first and second jaw members 150, 160 are laterally displaced with respect to each other to cut tissue disposed therebetween.

As discussed above, proximal movement of the trigger 184 causes a corresponding proximal movement of the longitudinal bar 186 which, in turn, moves the distal end portion 186*a* of the longitudinal bar 186 proximally and out of engagement with the intersection portions 116, 126 of the first and second shaft members 110, 120 such that the first and second shaft members 110, 120 are free to rotate about the "x" and "y" axes. At the same time, the proximal end portion 186*b* of the longitudinal bar 186 moves proximally such that the second guide member 188 engages the first guide member 136 of the first shaft member 110. Specifically, the angled wall 188*c* of the second guide member 188 contacts and slides against the angled wall 136*c* of the first guide member 136 thereby causing the first shaft member 110 to rotate about the "y" axis relative to the second shaft member 120, closing the gap "G" between the intersection portions 116, 126 of the first and second shaft members 110, 120, and laterally displacing the first and second jaw members 150, 160 relative to each other such that the shear edges 154, 164 of the first and second jaws 150, 160 cut the tissue disposed between the first and second jaw members 150, 160. Cutting is effected, for example, by the application of pressure on the tissue between the first and second jaw members 150, 160, and lateral movement of the shear edges 152*d*, 162*d* of the first and second tissue contacting surfaces 152, 162 with respect to each other.

The trigger 184 is then release and returns to the biased distal position. The first and second shaft members 110, 120 may then be moved back to the open position.

The embodiments disclosed herein may also be configured to work with robotic surgical systems and what is commonly referred to as "Telesurgery." Such systems employ various robotic elements to assist the operator and allow remote operation (or partial remote operation) of surgical instrumentation. Various robotic arms, gears, cams, pulleys, electric and mechanical motors, etc. may be employed for this purpose and may be designed with a robotic surgical system to assist the operator during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep a subject for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 15:
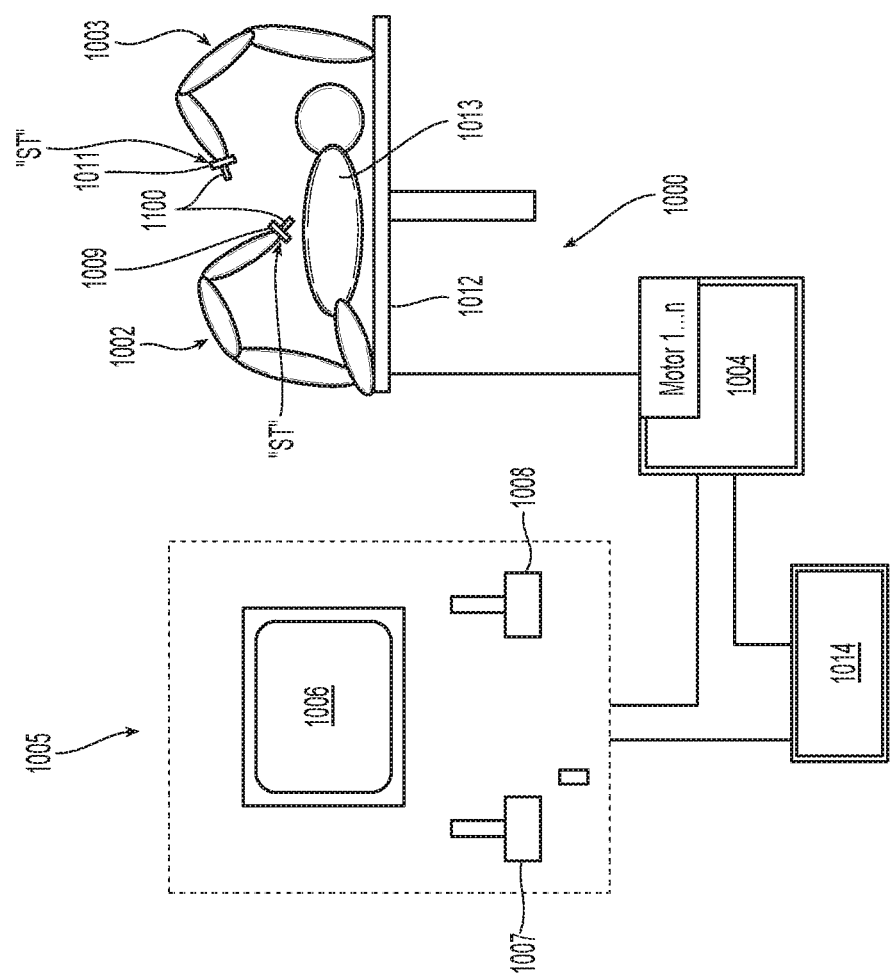
FIG. 15 is a schematic illustration of a work station configured for use with an electrosurgical instrument of the present disclosure.

Referring now to FIG. 15, a medical work station is shown generally as work station 1000 and generally may include: a plurality of robot arms 1002 and 1003; a control device 1004; and an operating console 1005 coupled with the control device 1004. The operating console 1005 may include a display device 1006, which may be set up in particular to display three-dimensional images; and manual input devices 1007 and 1008, by means of which an operator (not shown), for example a surgeon, may be able to tele-manipulate the robot arms 1002 and 1003 in a first operating mode.

Each of the robot arms 1002 and 1003 may include a plurality of members, which are connected through joints, and an attaching device 1009 and 1011, to which may be attached, for example, a surgical tool "ST" supporting an end effector 1100, in accordance with any one of several embodiments disclosed herein, as will be described in greater detail below.

The robot arms 1002 and 1003 may be driven by electric drives (not shown) that are connected to the control device 1004. The control device 1004 (e.g., a computer) may be set up to activate the drives, in particular by means of a computer program, in such a way that the robot arms 1002 and 1003, their attaching devices 1009 and 1011 and thus the surgical tool "ST" (including the end effector 1100) execute a desired movement according to a movement defined by means of the manual input devices 1007 and 1008. The control device 1004 may also be set up in such a way that it regulates the movement of the robot arms 1002 and 1003, and/or of the drives.

The medical work station 1000 may be configured for use on a patient 1013 lying on a patient table 1012 to be treated in a minimally invasive manner by means of the end effector 1100. The medical work station 1000 may also include more than two robot arms 1002 and 1003, the additional robot arms likewise being connected to the control device 1004 and being telemanipulatable by means of the operating console 1005. A medical instrument or surgical tool "ST" (including the end effector 1100) may also be attached to the additional robot arm. The medical work station 1000 may include a database 1014, in particular coupled to the control device 1004, in which are stored, for example, pre-operative data from patient/living being 1013 and/or anatomical atlases.

While several embodiments of the disclosure have been shown in the drawings and described herein, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

The invention claimed is:

1. An electrosurgical instrument, comprising:
a first shaft member including a proximal portion having a first handle member and a distal portion including a first jaw member;
a second shaft member coupled to the first shaft member about a pivot, the second shaft member including a proximal portion having a second handle member and a distal portion including a second jaw member; and
a trigger assembly disposed on the second shaft member, the trigger assembly including a housing supporting a trigger movable relative to the housing,
the first and second shaft members defining a longitudinal axis extending through the pivot, and first and second pivot axes that are substantially orthogonal to each other and the longitudinal axis, wherein at least one of the first or second handle members is pivotable about the first pivot axis to move the first and second jaw members, which are disposed in opposed and aligned relation to each other, to an open position, a grasping position, or a sealing position, and the trigger is movable to pivot at least one of the first or second shaft members about the second pivot axis to laterally displace the first and second jaw members relative to each other to a cutting position.

2. The electrosurgical instrument according to claim 1, wherein the trigger is longitudinally slidable relative to the housing between a proximal position and a distal position.

3. The electrosurgical instrument according to claim 2, wherein the trigger is biased in the distal position.

4. The electrosurgical instrument according to claim 2, wherein the trigger assembly includes a longitudinal bar disposed within the housing and secured to the trigger such that longitudinal movement of the trigger causes a corresponding longitudinal movement of the longitudinal bar.

5. The electrosurgical instrument according to claim 4, wherein the longitudinal bar includes a distal end portion movable in and out of engagement with intersection portions of the first and second shaft members.

6. The electrosurgical instrument according to claim 5, wherein when the trigger is disposed in the distal position, the distal end portion of the longitudinal bar is disposed between the intersection portions of the first and second shaft members such that the first and second shaft members are only pivotable about the first pivot axis.

7. The electrosurgical instrument according to claim 5, wherein when the trigger is disposed in the proximal position, the distal end portion of the longitudinal bar is proximal to the intersection portions of the first and second shaft members such that the first and second shaft members are pivotable about the first and second pivot axes.

8. The electrosurgical instrument according to claim 4, where the first shaft member includes a first guide member, and the longitudinal bar of the trigger assembly includes a proximal end portion having a second guide member movable in and out of engagement with the first guide member.

9. The electrosurgical instrument according to claim 8, wherein the first and second guide members each have an angled wall having complementary slopes, the angled walls disposed in opposed spaced relation relative to each other when the first and second jaw members are disposed in the sealing position and the trigger is disposed in the distal position.

10. The electrosurgical instrument according to claim 9, wherein when the trigger is actuated to the proximal position, the angled walls of the first and second guide members slidably engage each other and a force produced by proximal movement of the second guide member against the first guide member moves the first shaft member about the second pivot axis.

11. The electrosurgical instrument according to claim 10, wherein the first and second guide members each include a body portion and a leg portion having complementary L-shaped configurations, the leg portions of the first and second guide members configured to engage each other and limit movement of the first shaft member about the first pivot axis when the trigger is actuated to the proximal position.

12. The electrosurgical instrument according to claim 1, further comprising a connector assembly including a housing selectively engageable with the second elongated shaft member, the connector assembly configured to communicate electrosurgical energy between the first and second jaw members when in the sealing position.

13. The electrosurgical instrument according to claim 1, wherein the first and second jaw members each include a tissue contacting surface having a shear edge.

14. The electrosurgical instrument according to claim 1, wherein the pivot extends through intersection portions of the first and second shaft members, the intersection portions each including a substantially flat distal portion that is substantially flush with one another when the at least one of the first or second handle members is pivoted about the first pivot axis.

15. The electrosurgical instrument according to claim 14, wherein the intersection portion of the first shaft member includes an angled proximal portion defining a gap between the intersections portions, and wherein when the at least one of the first or second shaft members is pivoted about the second pivot axis the gap is closed.

16. The electrosurgical instrument according to claim 15, wherein the intersection portion of the second shaft member includes an insulative shim.

17. A method of treating tissue, comprising:
pivoting at least one of first or second handle members of respective first or second shaft members of an electrosurgical instrument about a first pivot axis that is orthogonal to a longitudinal axis defined through a pivot of the electrosurgical instrument to effect movement of first and second jaw members of the electrosurgical instrument to a sealing position in which the first and second jaw members are opposed and aligned with one another; and
actuating a trigger supported on a housing of a trigger assembly disposed on the second shaft member of the electrosurgical instrument to pivot at least one of the first or second shaft members about a second pivot axis that is transverse to the first pivot axis and the longitudinal axis to effect movement of the first and second jaw members from the sealing position to a cutting position in which the first and second jaw members are laterally displaced with respect to one another.

* * * * *